United States Patent [19]

Morton et al.

[11] 4,425,323

[45] Jan. 10, 1984

[54] SMOOTH DENTAL CREAM

[75] Inventors: Anthony J. Morton, Ashton-Under-Lyme; Kenneth Harvey, Wilmslow, both of England; Hermann Gutenberg, Gossau, Switzerland

[73] Assignee: Colgate-Palmolive Company, New York, N.Y.

[21] Appl. No.: 479,781

[22] Filed: Mar. 28, 1983

[51] Int. Cl.³ .......................... A61K 7/16; A61K 7/18
[52] U.S. Cl. ........................................ 424/52; 424/49; 424/57
[58] Field of Search ..................... 424/49–58

[56] References Cited

U.S. PATENT DOCUMENTS

| | | | |
|---|---|---|---|
| 3,070,510 | 12/1962 | Cooley et al. | 424/52 |
| 3,337,412 | 8/1967 | Elbreder | 424/151 |
| 3,903,252 | 9/1975 | Stearns et al. | 424/49 |
| 3,946,108 | 3/1976 | Tomlinson et al. | 424/49 |
| 4,020,154 | 4/1977 | Perla et al. | 424/49 |
| 4,022,881 | 5/1977 | Hawkins | 424/49 |
| 4,132,771 | 1/1979 | Schreiber et al. | 424/52 |
| 4,251,507 | 2/1981 | Olson | 424/49 |
| 4,344,931 | 8/1982 | Aguilar | 424/52 |

*Primary Examiner*—Shep K. Rose
*Attorney, Agent, or Firm*—Robert L. Stone; Murray M. Grill; Herbert S. Sylvester

[57] ABSTRACT

A dental cream containing high viscosity hydroxyethyl cellulose gelling agent, a calcium phosphate polishing agent and a binary source of fluorine of sodium fluoride and sodium monofluorophosphate.

6 Claims, No Drawings

SMOOTH DENTAL CREAM

This invention relates to a dental cream having desirable rheological properties.

Sodium carboxymethyl cellulose has commonly been used as a gelling agent of commercial choice in dental creams in view of its availability and the generally satisfactory rheological properties it gives to dental creams, particularly when they are made and used in temperate climates.

However it does have some disadvantages, such as being subject to decomposition by cellulase, particularly in tropical climates. Also, in certain dental creams such as those containing a binary source of fluorine from sodium monofluorophosphate and sodium fluoride and dicalcium phosphate polishing agent, dental creams formulated with many grades of sodium carboxymethyl cellulose become rough (soft lump or chunk formulation) in appearance even at room temperature, particularly when subject to dynamic aging, (that is extrusion for 2 cm of dental cream ribbon from a tube twice a day for 2 weeks, a condition which simulates normal use of a dental cream by a single person) and/or have poor "stand-up" qualities, that is, the rapid settling of the extruded cream into a flat ribbon.

Hydroxyethyl cellulose has been suggested as an alternative gelling agent to sodium carboxymethyl cellulose and indeed grades of hydroxyethyl cellulose such as Natrosol M have been used in commercial dental creams and grades have been set forth, for instance, in U.S. Pat. Nos. 3,862,207 (Natrosol G), and 3,070,510 (viscosity of 75–125 cps-Brookfield; 20° C.; 2%) and 4,022,881 (Natrosol 250H). Low viscosity grades of hydroxyethyl cellulose as described in U.S. Pat. Nos. 3,862,207 and 3,070,510, while generally satisfactory do tend to cause dental creams to form a visible "tail" upon extrusion onto a toothbrush.

In U.S. Pat. No. 4,022,881 a toothpaste was described containing as the thickening agent 5–30% of high viscosity hydroxyethyl cellulose (i.e. Natrosol 250H) and 70–95% sodium carboxymethyl cellulose to avoid forming a toothpaste with a "stringy" texture, which would occur if the hydroxyethyl cellulose were used in above 30% of the thickening agent. Various "abrasives" including "calcium phosphates" are mentioned as "typical toothpaste abrasives". However, except for calcium carbonate, none are actually set forth in toothpaste. In view of the disclosure of this patent, it would not be expected that dental creams containing polishing agent consisting essentially of a calcium phosphate with a gelling agent consisting essentially of high viscosity hydroxyethyl cellulose would have desirable rheological properties such as lack of string (tail) formation.

It is noteworthy that roughening on dynamic aging is particularly observable when the dental cream contains a compound which provides fluorine and a calcium phosphate is present as polishing material. Thus, there is little problem when fluorine is provided from sodium monofluorophosphate and sodium fluoride and the polishing agent is a siliceous material. However, the problem is readily observable when fluorine is provided from sodium monofluorophosphate or a mixture of sodium monofluorophosphate and sodium fluoride in a dental cream containing at least about 35% by weight of a calcium phosphate polishing material such as dicalcium phosphate.

Attempts to overcome the roughening problem without having other problems such as poor "stand up" occur by mixing different grades of sodium carboxymethyl cellulose or mixing different grades of sodium carboxymethyl cellulose with other gelling agents such as synthetic inorganic silicated clay (e.g. materials available under the trademarks "Laponite" and "Veegum"), thickeners such as silica thickeners available from Huber under the trademark "Zeosyl" as Zeosyl 200 and from Rhone Poulenc as Tixosil and as Tixosil 33J or available from Wacker under the identification "HDK N20", and liquid phase material such as polyethylene glycol 600 have not been satisfactory.

In copending commonly assigned application U.S. Ser. No. 417,941 filed Sept. 14, 1982 by Anthony John Morton and Kenneth Harvey, dental cream is described in which there is little susceptibility to roughness upon aging together with other desirable rhelogical properties such as good "stand up", absence of formation of a "tail" on an extruded ribbon of dental cream and good ribbon gloss. That dental cream contains a gelling agent mixture of sodium carboxymethyl cellulose and hydroxyethyl cellulose, each being present in a weight ratio of about 3:2 to 2:3.

It has now been found that desirable rheological properties of a dentifrice containing a binary source of fluorine from sodium monofluorophosphate and sodium fluoride and a calcium phosphate polishing agent are attained with gelling agent of high viscosity hydroxyethyl cellulose is employed. When the hydroxyethyl cellulose is present, it is not necessary to mix it with sodium carboxymethyl cellulose or other gelling agent.

It is an advantage of this invention that high viscosity hydroxyethyl cellulose gelling agent is provided which does not cause a dental cream containing a binary fluorine system and dicalcium phosphate polishing agent to form a tail.

Other advantages will be apparent from consideration of the following specification.

In accordance with certain of its aspects, this invention relates to a dental cream comprising a binary fluorine source of a mixture of sodium monofluorophosphate and sodium fluorine in which about 30–40% by weight of said fluorine is from said sodium fluoride in amount to provide about 750–2000 ppm total of ionic fluorine about 35–75% by weight of a polishing agent consisting essentially of a calcium phosphate and a dental vehicle comprising about 20–80% by weight based on the weight of the dental cream of a liquid phase containing water, humectant or mixture thereof and about 0.5–5% by weight based on the weight of the dental cream of a gelling agent consisting essentially of hydroxyethyl cellulose having a viscosity of in a range the average of which is at least about 24,000 cps, determined on a Brookfield viscometer in 2% water: glycerine (1:1,56) solution at 20° C., with a No. 6 spindle at 20 rpm.

The gelling agent is present in the dental cream in amount of about 0.5–5% by weight, preferably about 0.8–2%, and most preferably about 0.9–1.1%. A grade of hydroxyethyl cellulose effective in the practice of the present invention is Tylose H 10000P, available from Farbwerke Hoechst of Frankfurt am Main, Germany.

Tylose H 10,000P and other grades of hydroxyethyl cellulose in accordance with the present invention have viscosities in a range the average of which is at least about 24,000 cps. In the present specification viscosity values are determined on a Brookfield viscometer at 20°

C., in a water: glycerine (1:1,56) solution with a No. 6 spindle at 20 rpm. Hydroxyethyl cellulose grades which may be used in the present invention are set forth in the following table:

TABLE

| SUPPLIER | HEC GRADE | VISCOSITY |
|---|---|---|
| Hercules | Natrosol 250 HR and 250 H | 17000–31000 |
| | Natrosol 250 HHR and 250 HH | 37000–41000 |
| Hoechst | Tylose H 10000P | 20000–30000 |

Hydroxyethyl cellulose grades of viscosity not reaching an average of about 24,000 cps, such as Hercules 250M and MR (average viscosity of 15,500 cps) and Hoechst Tylose 4000P (viscosity of up to 23,000 cps), do not provide the desired rheology when used as the only gelling agent.

In the dental cream formulation the dental vehicle comprises a liquid phase proportioned with the gelling agents to form an extrudible creamy mass of desirable consistency. In general, liquids in the dental cream will comprise chiefly water, glycerine, sorbitol, polyethylene glycol 400, propylene glycol, or the like including suitable mixtures thereof. It is advantageous usually to use a mixture of both water and a humectant or binder such as glycerine or sorbitol; typically about 10–30% by weight of water and about 20–50% by weight of humectant. It is preferred to use glycerine. The total liquid content will generally be about 20–80% by weight of the formulation.

The dental creams contain a binary fluorine source providing about 750–2000 ppm of fluorine from a mixture of sodium monofluorophosphate and sodium fluoride wherein about 30–40% of said fluorine is from sodium fluoride. A preferred amount of fluorine is about 1400–2000 ppm, particularly about 1400–1670 ppm.

Sodium monofluorophosphate, $Na_2PO_3F$, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble phosphate salt. Expressed in another way, the sodium monofluorophosphate employed should have a total fluoride content of about 12%, preferably above 12.7%, a content of not more than 1.5%, preferably not more than 1.2% of free sodium fluoride; and a sodium monofluorophosphate content of at least 12%; preferably at least 12.1% all calculated as fluoride.

Sodium fluoride in the binary mixture is a separate fluorine-containing component from sodium monofluorophosphate. About 300–580 ppm of fluorine is preferably provided to the dental cream by sodium fluoride.

The dental cream typically contains about 35–75% by weight, preferably 40–55% of a dentally acceptable water-insoluble polishing material which consists essentially of a calcium phosphate, such as dicalcium phosphate in its dihydrated or anhydrous forms or as mixtures thereof in any desired ratio, tricalcium phosphate and calcium pyrophosphate. Most typically dicalcium phosphate is employed, generally as the dihydrate. Dicalcium phosphate is typically the sole polishing agent, but if desired minor amounts (e.g. up to about 5% by weight of the dental cream and up to about 12% by weight of the total polishing material) of other dentally acceptable water-insoluble polishing agents which do not substantially interfere with the ability of the composition of the invention to promote oral hygiene may be present. Typical polishing agents are alumina, silica, sodium aluminosilicate etc. A minor amount of hydrated alumina (e.g. about 1%) also inhibits or even eliminates the tendency of some dental creams to separate or "bleed" in their tubes.

The gelling agent system of the present invention is particularly desirable as the gelling component of dental creams containing the binary fluorine mixture and dicalcium phosphate polishing agent described in commonly assigned printed British Patent Specification No. 20 68 727 A (Application 79/43642), the disclosure of which is incorporated herein by reference. Thus, in a typical dental cream, sodium monofluorophosphate is typically used in the binary system in amount to provide about 700–1090 ppm fluorine to the dental cream in which the total amount of fluorine is about 1000–1670 ppm with about 30–35% weight to the total fluorine being provided by sodium fluoride (about 300–580 ppm). This corresponds to about 0.5–1.2% by weight of sodium monofluorophosphate and about 0.05–0.11% by weight of sodium fluoride. Preferably, the dental cream thereof contains about 1000–1500 ppm, most preferably, about 950–1000 ppm fluorine provided by sodium monofluorophosphate and about 450–500 ppm provided by sodium fluoride.

Any suitable surface active or detersive material may be included in the dentifrice compositions. Such compatible materials are desirable to provide additional detersive, foaming and antibacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g., sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Various other materials may be incorporated in the dental creams of this invention. Examples thereof are colouring or whitening agents, preservatives, stabilizers, tetrasodium pyrophosphate, silicones, chlorophyll compounds and ammoniated materials such as urea, diammonium phosphate and mixtures thereof. These adjuvants are incorporated in the instant compositions in amounts which do not substantially adversely affect the desired properties and characteristics and are suitably selected and used in conventional amounts.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4-(chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis (2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalpytus, marjoram, cinnamon, lemon and orange, as well as methylsalicylate. Suitable sweetening agents include sucrose, lactose, maltose, sorbitol, sodium cyclamate, sodium saccharine, dipeptides of U.S. Pat. No. 3,939,261 and oxathiazin salts of U.S. Pat. No. 3,932,606. Suitable, flavour and sweetening agent may together comprise from about 0.01 to 5% or more of the composition.

The dental creams should have a pH practicable for use. A pH range of 5 to 9 is particularly desirable. The reference to the pH is meant to be the pH determination directly on the toothpastes. If desired, materials such as benzoic acid or citric acid may be added to adjust the pH to, say, 5.5 to 6.5.

The dental cream is typically packaged in an extrudible tube, such as lined or unlined aluminum or lead, or laminate tubes.

The following example is further illustrative of the nature of the present invention, but it is to be understood that the invention is not limited thereto. The compositions are prepared in the usual manner and all amounts of the various ingredients are by weight unless otherwise specified.

EXAMPLE

The following dental cream is prepared by conventional dental cream formulation technique, placed in an aluminium dental cream tube and extruded by extruding dental cream ribbon twice a day, five days a week for two weeks:

|  | PARTS |
|---|---|
| Glycerine | 22.00 |
| Hydroxyethyl cellulose-viscosity 20000–30000 (Hoechst Tylose H10000P) | 1.00 |
| Dicalcium phosphate dihydrate | 48.00 |
| Sodium lauryl sulphate | 1.50 |
| Sodium saccharine | 0.20 |
| Sodium monofluorophosphate | 0.76 |
| Sodium fluoride | 0.10 |
| Flavour | 0.90 |
| Deionized water | Q.S. to 100 |

The dental cream does not form a tail upon extrusion and is rheologically desirable.

The rheology is also desirable when Tylose H10000P is replaced by Natrosol 250H and by Natrosol 250HH.

When lower viscosity grades of hydroxyethyl cellulose such as Natrosol 250M (Hercules) and Tylose H4000P replace Tylose H10000P, a tail forms upon extrusion of the dental cream.

Although the invention has been described with regard to a specific example and certain variations thereof, it will be apparent to one skilled in the art that various modifications may be made thereto which fall within its scope.

We claim:

1. A dental cream which does not form a tail upon extrusion comprising a binary fluorine source of a mixture of sodium monofluorophosphate and sodium fluoride in which about 30–40% by weight of said fluorine is from said sodium fluoride, in amount to provide about 750–2000 ppm total of ionic fluorine, about 35–75% by weight of a polishing agent consisting essentially of a calcium phosphate and a dental vehicle comprising about 20–80% by weight based on the weight of the dental cream of a liquid phase containing water, humectant or mixture thereof and about 0.5–5% by weight based on the weight of the dental cream of a gelling agent consisting essentially of hydroxyethyl cellulose having a viscosity in a range the average of which is at least, about 24,000 cps, determined on a Brookfield viscometer in 2% water:glycerine (1:1.56) aqueous solution at 20° C., with a No. 6 spindle at 20 rpm.

2. The dental cream claimed in claim 1 wherein said gelling agent is present in amount of about 0.8–2% by weight.

3. The dental cream claimed in claim 1 wherein said binary fluorine source provides about 1400–2000 ppm of ionic fluorine.

4. The dental cream claimed in claim 1 wherein dicalcium phosphate is present as polishing agent in amount of about 40–75% by weight.

5. The dental cream claimed in claim 1 wherein said hydroxyethyl cellulose is a grade having a viscosity of about 17,000–31,000; about 37,000–41,000 or about 20,000–30,000.

6. The dental cream claimed in claim 5 wherein said hydroxyethyl cellulose has a viscosity of about 20,000–30,000.

* * * * *